(12) United States Patent
Park et al.

(10) Patent No.: US 7,544,472 B2
(45) Date of Patent: Jun. 9, 2009

(54) APPARATUS FOR DETECTING BIOMOLECULAR BONDING AND A METHOD THEREOF

(75) Inventors: Tae-sik Park, Suwon-si (KR); Young-il Kim, Suwon-si (KR); Jung-ho Kang, Suwon-si (KR)

(73) Assignee: Samsung Electronics Co., Ltd. (KR)

( * ) Notice: Subject to any disclaimer, the term of this patent is extended or adjusted under 35 U.S.C. 154(b) by 307 days.

(21) Appl. No.: 11/325,056

(22) Filed: Jan. 3, 2006

(65) Prior Publication Data

US 2006/0147972 A1    Jul. 6, 2006

(30) Foreign Application Priority Data

Jan. 3, 2005    (KR) ...................... 10-2005-0000149

(51) Int. Cl.
*C12Q 1/68* (2006.01)
*C12M 1/36* (2006.01)
*G01N 15/06* (2006.01)

(52) U.S. Cl. ...................... 435/6; 435/283.1; 435/287.2; 435/288.7; 422/64; 422/68.1; 422/82.05

(58) Field of Classification Search ...................... None
See application file for complete search history.

(56) References Cited

U.S. PATENT DOCUMENTS

| 5,413,939 | A  | * | 5/1995  | Gustafson et al. ........... 436/518 |
| 6,319,468 | B1 | * | 11/2001 | Sheppard et al. ............. 422/63  |
| 2001/0040130 | A1 | * | 11/2001 | Lorch et al. .................. 210/601 |
| 2002/0055111 | A1 | * | 5/2002  | Chen et al. ..................... 435/6 |

* cited by examiner

*Primary Examiner*—BJ Forman
(74) *Attorney, Agent, or Firm*—Cantor Colburn LLP

(57) ABSTRACT

An apparatus and method for detecting biomolecular bonding are disclosed. The apparatus comprises a substrate; a rotation unit mounted on the substrate, a probe biomolecule immobilized on a surface of the rotation unit; an input port and an output port connected with the substrate. A frequency detector is connected with the output port to measure rotational frequency of the rotation unit. The presence or absence of molecular bonding is detected by measuring difference between the rotational frequencies before and after mixing the probe biomolecule with a sample biomolecule.

15 Claims, 8 Drawing Sheets

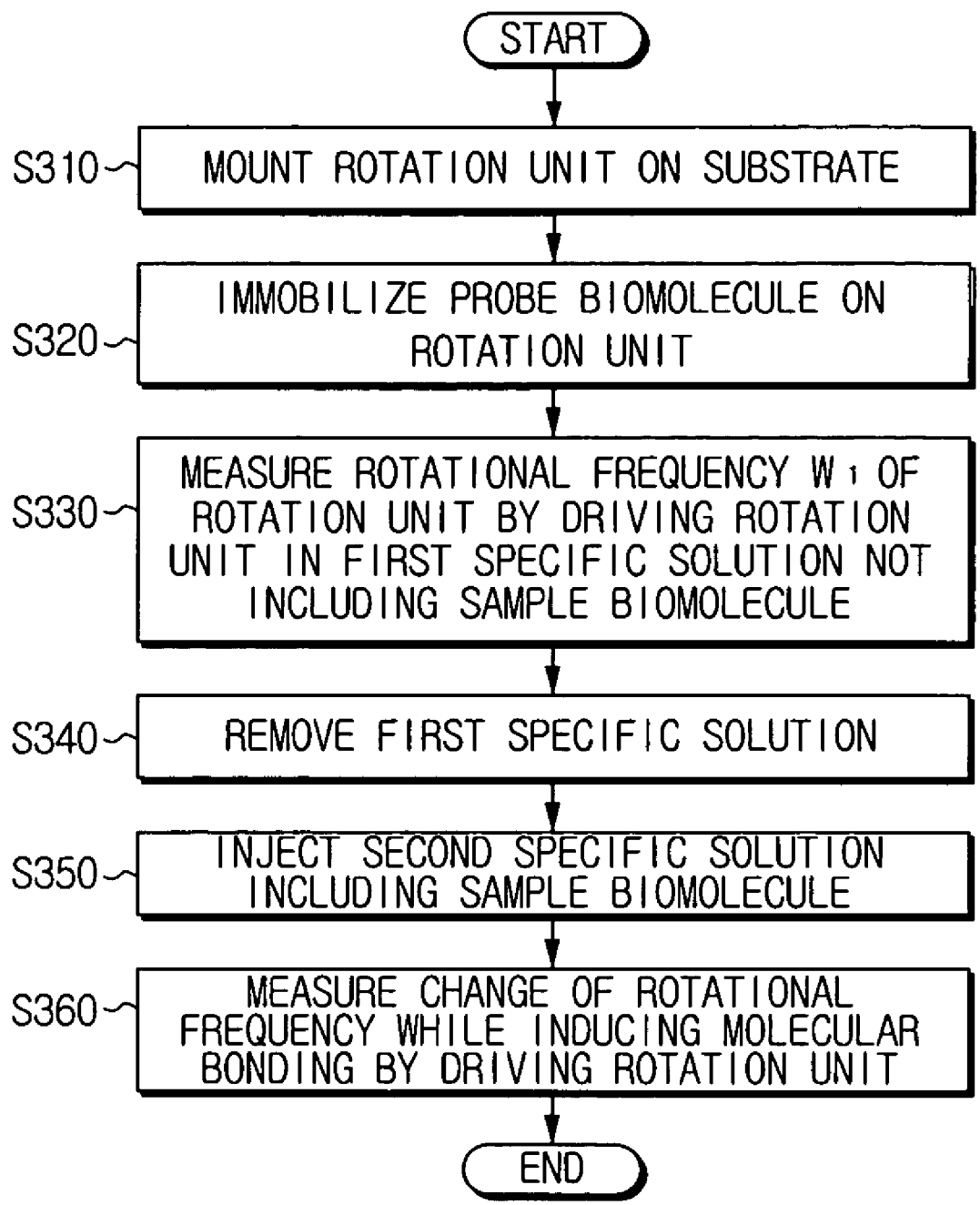

US 7,544,472 B2

APPARATUS FOR DETECTING BIOMOLECULAR BONDING AND A METHOD THEREOF

This application claims priority to Korean Patent Application No. 2005-00149, filed Jan. 3, 2005, and all the benefits accruing therefrom under 35 U.S.C. § 119, the content of which is herein incorporated by reference in its entirety.

BACKGROUND OF THE INVENTION

1. Field of the Invention

The present invention relates to an apparatus and method for detecting biomolecular bonding. More particularly, the present invention relates to an apparatus and method for detecting whether biomolecular bonding has been achieved, by monitoring frequency change before and after the biomolecular bonding.

2. Description of the Related Art

A biochip refers to a biological microchip comprising biomolecules such as deoxyribonucleic acid (DNA) sequences, DNA segments, ribonucleic acid (RNA) sequences, peptides and/or protein molecules which are immobilized at intervals on a small solid substrate. A biochip enables analysis of gene expression, genetic mutation, biomolecule defects, protein distribution, and like characteristics of an experimental sample. The substrate can be made, for example, of glass or silicon. A biomolecule immobilized on the surface of the biochip can function as a probe that searches molecular information included in an experimental sample. By mixing the biochip with an experimental sample to be analyzed, substances in the sample can bind with a probe fixed on the biochip surface. By detecting and analyzing the binding, information can be obtained on the substances in the experimental sample.

In order to determine whether an experimental sample includes a biomolecule capable of bonding with a probe biomolecule, a detection system is needed to detect bonding between the probe biomolecule and the sample biomolecule.

Existing signal detecting methods include, for example, a laser-induced fluorescence (LIF) detecting method, an electrochemical detecting method, or a mechanical detecting method. FIGS. 1A to 1D illustrate examples of conventional bio-bonding detecting systems and methods.

FIG. 1A is a view illustrating a conventional LIF detecting method. The LIF detecting method includes labeling a sample biomolecule with a fluorescent material. The sample biomolecule with the fluorescent label is mixed with the probe biomolecules, and any binding between the probe biomolecule and the sample biomolecule is determined optically with a confocal microscope or a charge coupled device (CCD) camera. This method, however, requires a pre-processing reaction for binding the fluorescent material to the sample biomolecule before the bonding reaction between the probe and the sample biomolecule, possibly causing loss or contamination of the sample biomolecule. Another disadvantage includes the requirement for a complicated, high-priced optical reader system to read the result of the bonding reaction between the probe biomolecules and the sample biomolecule. Additionally, the optical detection method makes it difficult to provide a compact sized optical detector, and a digitized output cannot be obtained.

FIG. 1B is a view of a conventional mechanical detector. The mechanical detecting method uses a micro-assembled cantilever to monitor intermolecular binding force before and after the bonding between the probe biomolecules and the sample biomolecule. However, this method requires precise monitoring of the deflection of the cantilever beam. Additionally, an instrument such as a laser or the like is also required.

FIGS. 1C and 1D each illustrate a conventional biomolecular-bonding detecting apparatus using a capacitance device. Specifically, FIG. C illustrates a biomolecular-bonding detecting apparatus using a trench-type capacitance device, and FIG. 1D illustrates a biomolecular-bonding detecting apparatus using a planar capacitance device.

In the case of detecting biomolecular-bonding using a capacitance device, there is a disadvantage in that it is difficult to form a compact-sized capacitance device. Since capacitance is proportional to cross-sectional area and is inversely proportional to thickness, a capacitance device is difficult to design to facilitate bio processing, since the cross-sectional area must be increased. In a biomolecular-bonding detecting apparatus using a trench-type capacitor as in FIG. 1C, a deep trench is formed so as to make the capacitor thinner and to enlarge the cross-sectional area thereof. In this case, however, there is a disadvantage in that the actual gap is very small, thus making it difficult to implement bio-processing. The biomolecular-bonding detecting apparatus of FIG. 1D using a capacitor similar to that formed as a comb shape in a plane, also has a disadvantage in that the thickness of a metallic thin film is so small that many capacitance devices cannot easily be formed on a metallic film, thereby resulting in poor sensitivity in detecting biomolecular-bonding between molecules.

SUMMARY OF THE INVENTION

In an exemplary embodiment, the present invention provides an apparatus and method for detecting biomolecular-bonding, in which a probe biomolecule is immobilized on a rotation unit, and the difference between rotational frequencies of the rotation unit before and after molecular bonding of the sample to the probe is measured to thereby detect whether the molecular bonding is achieved.

In an exemplary embodiment, an apparatus for detecting biomolecular-bonding includes a substrate, a rotation unit mounted on the substrate, the rotation unit having a probe biomolecule immobilized on a surface thereof. An input port is connected to the substrate, the input port configured to receive an input signal for driving the rotation unit. An output port is connected to the substrate, the output port configured to output an output signal indicative of the rotational frequency of the rotation unit. A frequency detector is in communication with the output port.

In another exemplary embodiment, the rotation unit rotates about a shaft unidirectionally or bidirectionally.

In another exemplary embodiment, the rotation unit is immobilized on the substrate by one end thereof and torsionally vibrated upon application of the input signal from the input port. The rotation unit includes, for example, a piezoelectric material.

In another exemplary embodiment, the probe biomolecule comprises at least one of a deoxyribonucleic acid (DNA), a ribonucleic acid (RNA), a protein, a cell, a nucleic acid, enzyme or a combination thereof.

In an exemplary embodiment, a method for detecting biomolecular-bonding is provided. The method includes mounting a rotation unit on a substrate, immobilizing a probe biomolecule on the rotation unit, and measuring a first rotational frequency $w_1$ of the rotation unit before bonding, by driving the rotation unit in a first specific solution in which a sample biomolecule is not included. The probe biomolecule is mixed with the sample biomolecule by driving the rotation unit in a second specific solution comprising the sample biomolecule.

A second rotational frequency $w_2$ of the rotation unit is measured after mixing the probe biomolecule with the sample biomolecule.

In some embodiments, the first and second rotational frequencies ($w_1$ and $w_2$) of the rotation unit are measured by driving the rotation unit in a first specific solution in which the sample biomolecule is not included.

In other embodiments, the mixing further includes removing the first specific solution from the rotation unit, supplying a second specific solution which comprises the sample biomolecule to the rotation unit, and driving the rotation unit such that bonding can occur between the probe biomolecule and the sample biomolecule.

The method may further include removing unbound sample biomolecules from the rotation unit.

In another exemplary embodiment, a method for detecting biomolecular-bonding includes mounting a rotation unit on a substrate, immobilizing a probe biomolecule on the rotation unit, and measuring a first rotational frequency $w_1$ of the rotation unit before bonding, by driving the rotation unit in a first specific solution in which a sample biomolecule is not included. The probe biomolecule is mixed with the sample biomolecule by driving the rotation unit in a second specific solution comprising the sample biomolecule, and a second rotational frequency $w_2$ of the rotation unit is measured after mixing the probe biomolecule with the sample biomolecule.

In some embodiments, the method may further include removing the first specific solution after measuring the first rotational frequency $w_1$.

BRIEF DESCRIPTION OF THE DRAWING FIGURES

The above aspect and other features of the present invention will become more apparent by describing certain exemplary embodiments of the present invention with reference to the attached drawing figures, wherein;

FIG. 6 is a flowchart illustrating a method for detecting biomolecular bonding according to another exemplary embodiment of the present invention.

DETAILED DESCRIPTION OF THE EXEMPLARY EMBODIMENTS

Figure 1A:
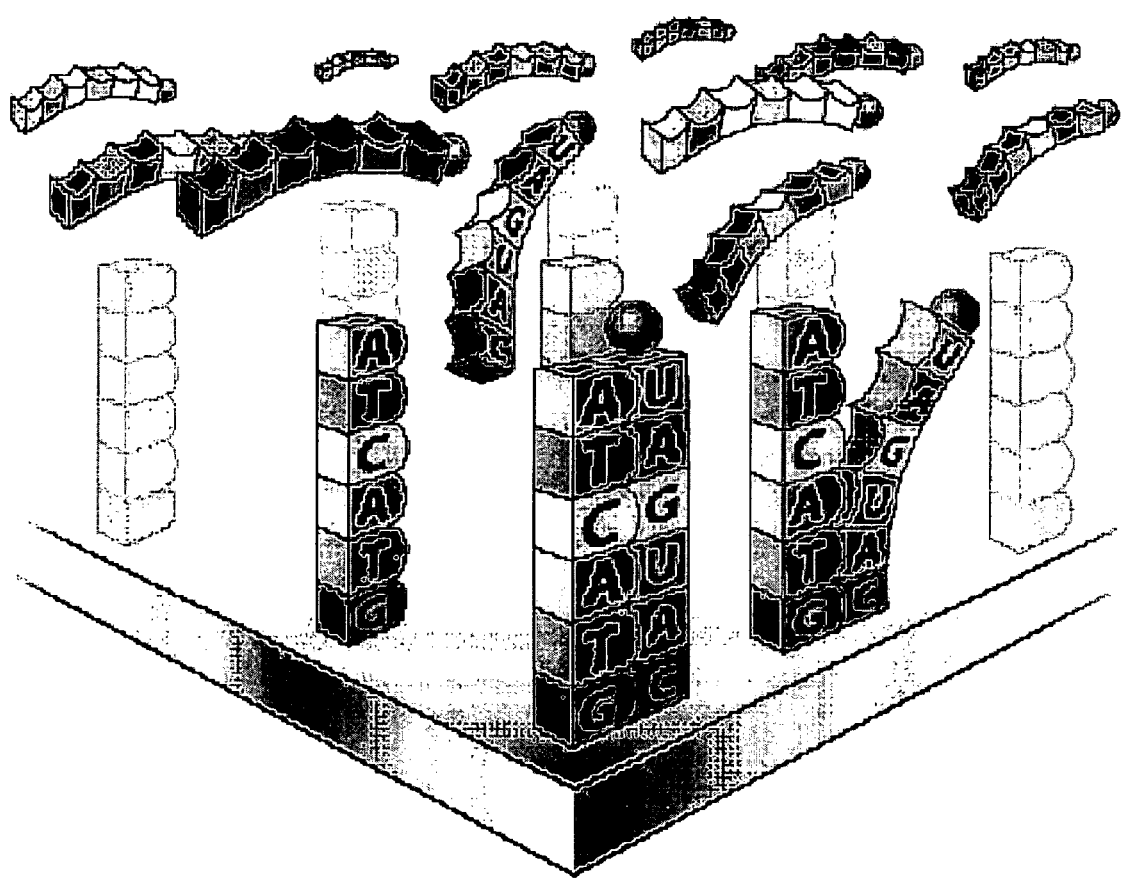
FIGS. 1A to 1D illustrate conventional systems and methods for detecting biomolecular bonding.
Figure 1B:
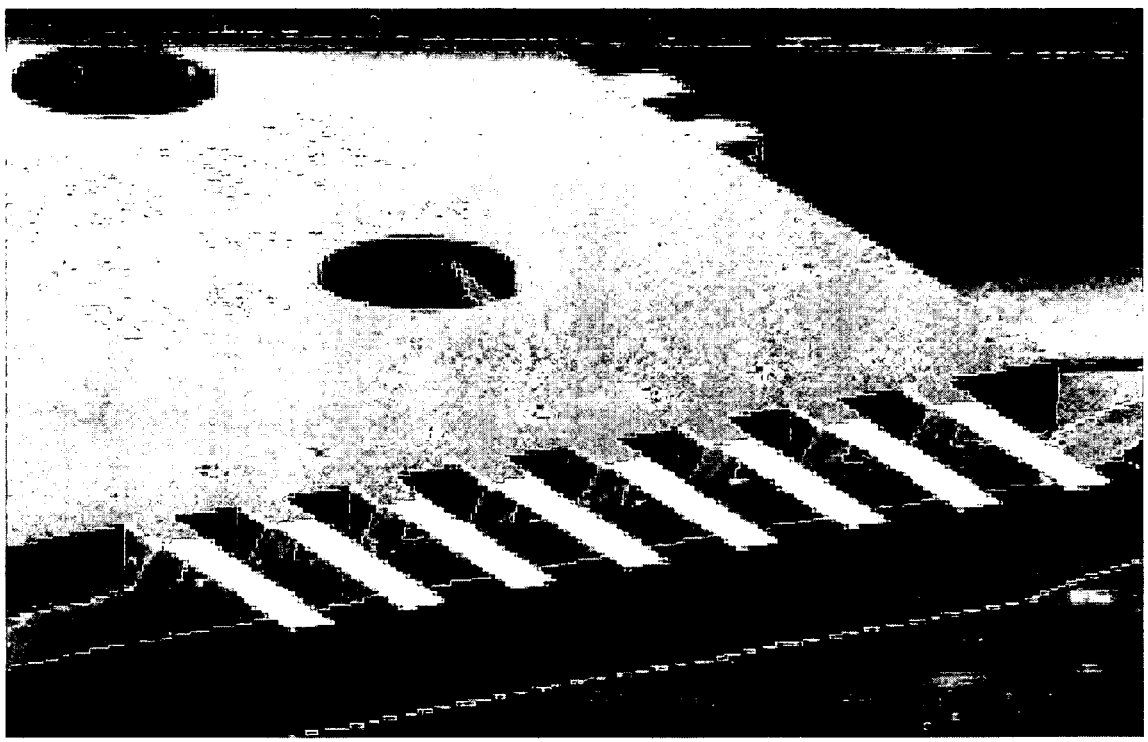
Figure 1C:
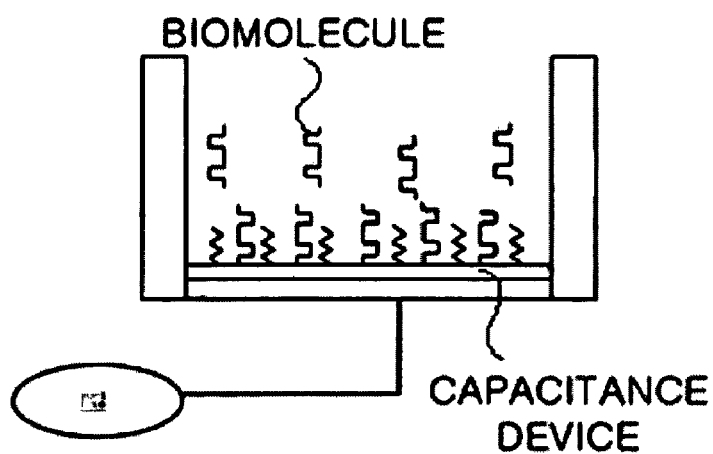
Figure 1D:
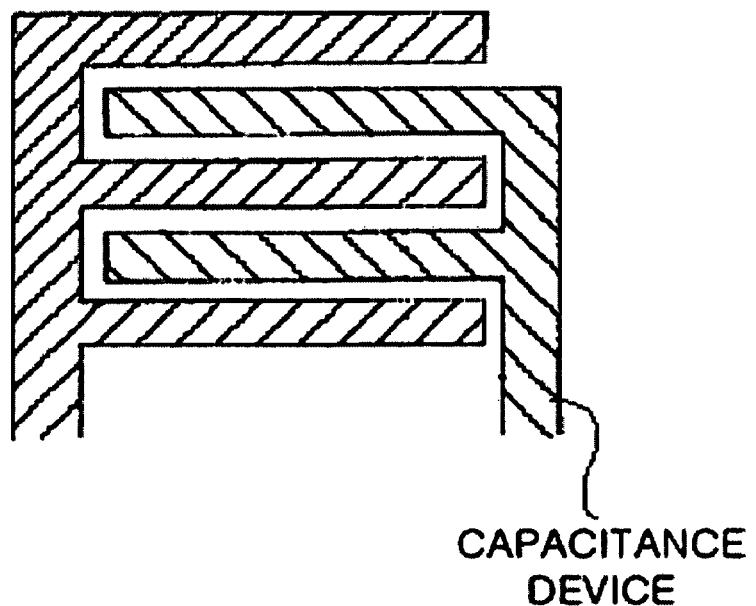

The invention is described more fully hereinafter with reference to the accompanying drawings, in which exemplary embodiments of the invention are shown. This invention can, however, be embodied in many different forms and should not be construed as limited to the exemplary embodiments set forth herein. Rather, these embodiments are provided so that this disclosure will be thorough and complete, and will fully convey the scope of the invention to those skilled in the art. Embodiments defined in the description, such as construction details and elements of the invention are provided to assist in a comprehensive understanding of the invention. Thus, it is apparent that the present invention can be carried out without those defined embodiments. Additionally, well-known functions or constructions are not described in detail since they would obscure the invention in unnecessary detail.

In the following description, identical drawing reference numerals are used for identifying identical elements, even for identical elements found in separate drawings. It will be understood that when an element or layer is referred to as being "on" or "connected to" another element or layer, the element or layer can be directly on or connected to another element or layer or intervening elements or layers. In contrast, when an element is referred to as being "directly on" or "directly connected to" another element or layer, there are no intervening elements or layers present. As used herein, the term "and/or" includes any and all combinations of one or more of the associated listed items. The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Figure 2:
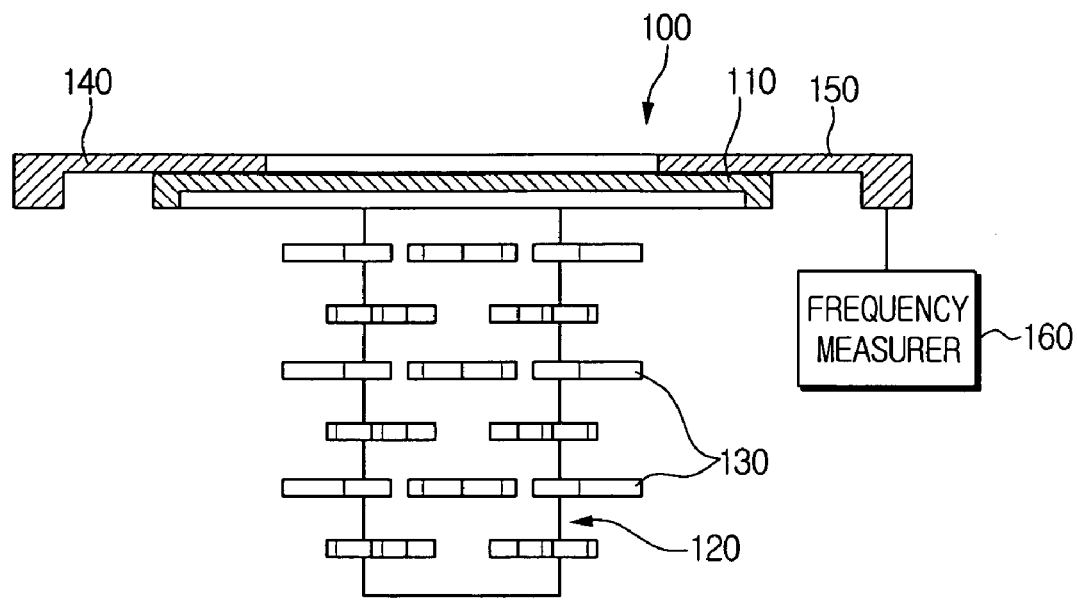
FIG. 2 illustrates an apparatus for detecting biomolecular bonding, according to one embodiment of the present invention.
Figure 3:
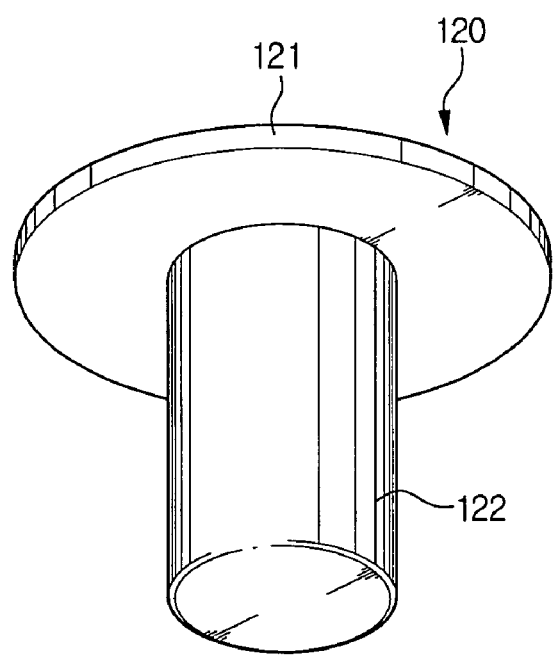
FIG. 3 illustrates an exemplary rotation unit of FIG. 2.

Referring initially to FIGS. 2 and 3, an apparatus for detecting biomolecular bonding includes a substrate 110, a rotation unit 120, an input port 140, an output port 150, and a frequency detector 160.

The rotation unit 120 is mounted on a predetermined area of the substrate 110, which can be formed in a wafer level.

The rotation unit 120 can be rotated about a rotation shaft by a motor (not shown). One or more probe biomolecules 130 are immobilized to the rotation unit 120 to detect specific information on a sample biomolecule to be analyzed. The rotation unit 120 comprises a support part 121 mounted on the substrate 110 and a pillar part 122 vertically protruding from the support part 121. The probe biomolecules 130 are immobilized on a surface of the pillar part 122. The pillar part 122 preferably has a cylindrical or a polygonal-pillar shape so as to reduce frictional resistance during rotation thereof. The rotation unit 120 can be rotated by a dedicated motor (not shown) in communication with the substrate 110 or by a rotor directly attached to the support part 121. The probe biomolecules 130, which can be, for example, deoxyribonucleic acid (DNA), ribonucleic acid (RNA), protein, cell, enzyme, nucleic acids, comprising at least one of the foregoing biomolecules thereof, can specifically bind with a sample biomolecule to be analyzed.

Upon binding of the sample biomolecule to the probe biomolecule, the mass and structure of the rotation unit changes. Therefore, the rotational frequency of the rotation unit 120 changes as a result of a change in viscosity, structure and mass of the rotation unit 120 accompanying binding. As described above for one embodiment of the present invention, one or more rotational based characteristics of the rotation unit 120 with an immobilized probe biomolecule 130 can therefore be monitored to determine the presence or absence of bonding between the probe biomolecule and a sample biomolecule. In particular, by measuring the rotational frequency of the rotation unit 120, a characteristic that can be easily measured, bonding between the probe biomolecule 130 and the sample biomolecule can be detected based on any difference in the rotational frequency measured before and after mixing the probe biomolecule with a sample.

Although the rotation unit 120 rotates about its central axis unidirectionally or bidirectionally in the exemplary embodiments depicted herein, the present invention is not limited so. For instance, instead of completely rotating the rotation unit 120, a rotary stick may be adopted and laterally twisted, allowing for measurement of torsional vibration. In this exemplary embodiment, one end of the rotary stick is immobilized on a substrate while the other end is periodically twisted clockwise and counterclockwise. Changes in the frequency of torsional vibration can by be measured before and after the probe biomolecule 130 has been exposed to the sample biomolecule, wherein the change in frequency determines whether bonding of the molecules occurred.

In one embodiment, the rotary stick includes a piezoelectric material, which generates electric energy (voltage) corresponding to mechanical energy exerted from the outside. Conversely, when electric energy is applied to the piezoelectric material, mechanical energy is generated. Furthermore, upon application of alternating current (AC) as the electric energy, piezoelectric material demonstrates specific vibrational frequencies.

When AC is applied to a rotary stick formed from a piezoelectric material that has been immobilized by one end to the substrate, the rotary stick torsionally vibrates. Accordingly, whether molecular bonding occurs can be detected through immobilizing one or more probe biomolecules to the rotary stick and thereafter measuring the vibrational frequency before and after mixing the probe biomolecule with the sample biomolecule.

In one exemplary embodiment, the input port 140 is connected to one side of the substrate 110 and inputs a signal for driving the rotation unit 120. The output port 150 is connected to the other side of the substrate 110 and outputs a signal corresponding to the rotational frequency of the rotation unit 120.

In another exemplary embodiment, the frequency detector 160 is connected to the output port 150. The frequency detector 160 measures the rotational frequency of the rotation unit 120. More specifically, the rotational frequency can be measured before and after mixing the probe biomolecule 130 immobilized to the rotation unit 120 and the sample biomolecule to be analyzed, and compared to determine whether bonding of the probe biomolecule and the sample biomolecule is present or absent.

Figure 4A:
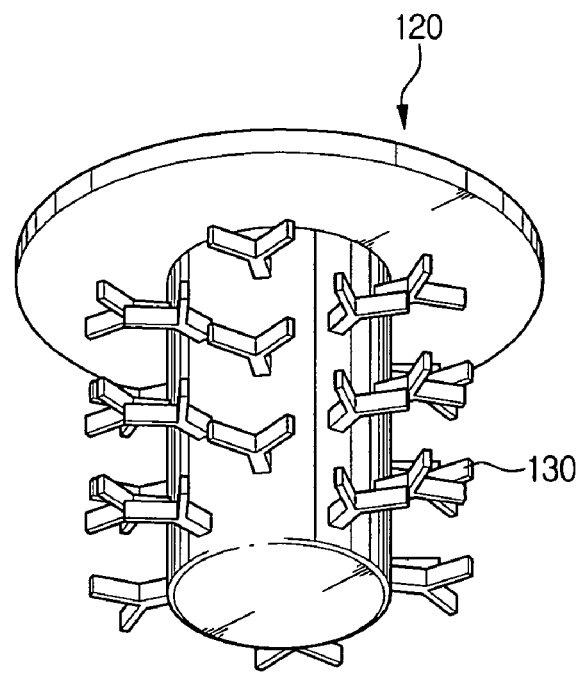
FIGS. 4A to 4C illustrates exemplary processes for detecting biomolecular bonding, according to one embodiment of the present invention.
Figure 4B:
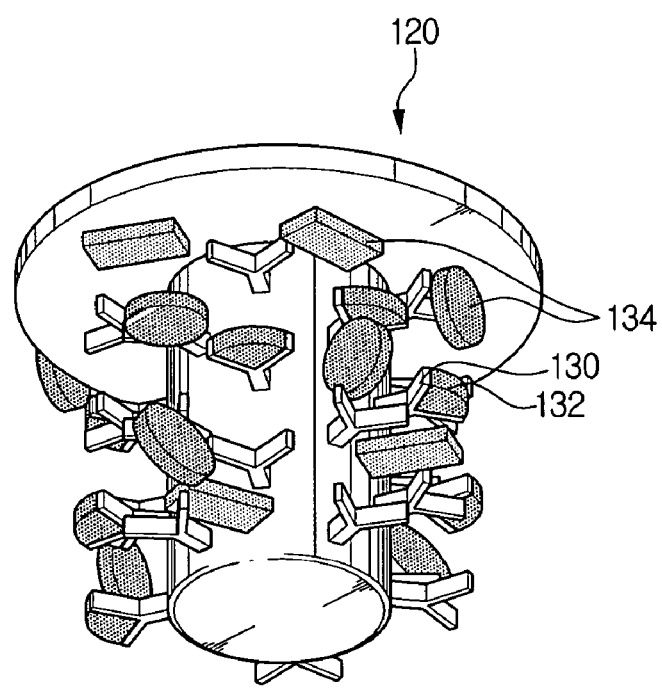
Figure 4C:
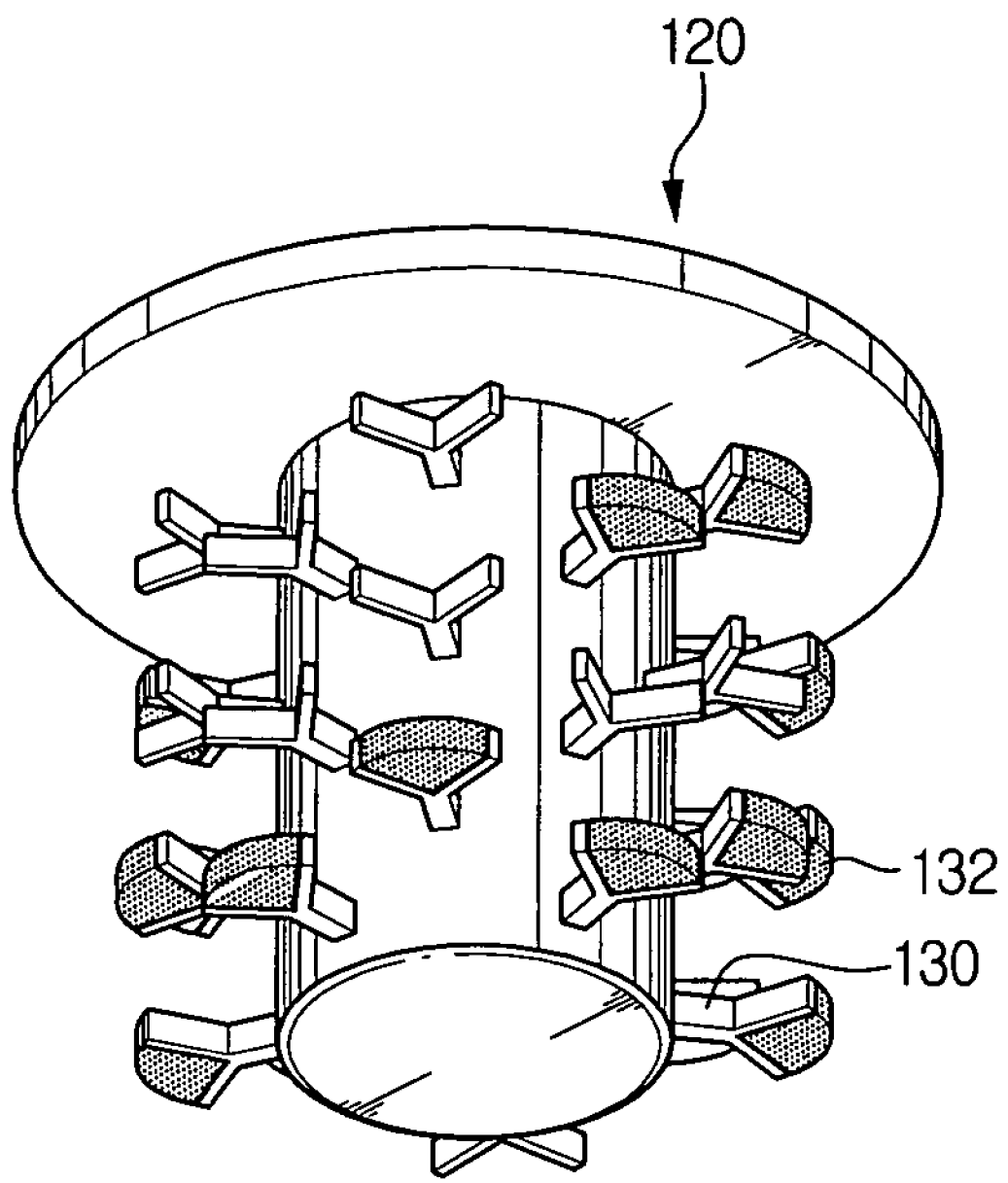

FIGS. 4A through 4C are illustrative views of the rotation unit to aid in the explanation of the processes for detecting biomolecular bonding according to an exemplary embodiment of the present invention.

Figure 5:
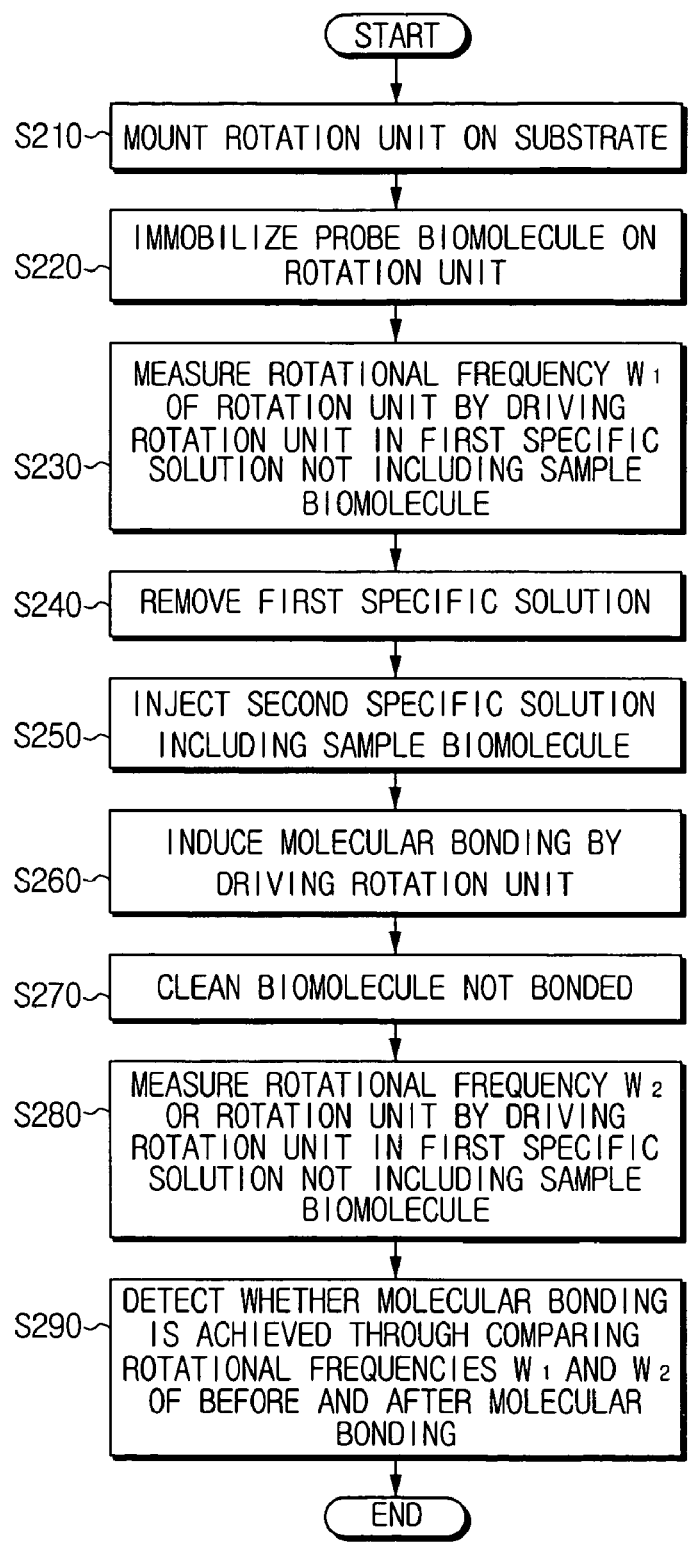
FIG. 5 is a flowchart illustrating a method for detecting biomolecular bonding according to an exemplary embodiment of the present invention.

FIG. 5 is a flowchart illustrating a method for detecting biomolecular-bonding according to an exemplary embodiment of the present invention. Hereinafter, a method for detecting the biomolecular bonding will be described with reference to FIGS. 4A to 5.

In one embodiment, the rotation unit 120 is mounted on a predetermined area of the substrate 110 (operation S210). The probe biomolecule 130 is immobilized on the rotation unit 120 (S220). As the particular method for immobilizing the probe biomolecule 130 is not an essential feature of the present disclosure, it is therefore not described in further detail herein.

The rotational frequency of the rotation unit 120 is measured prior to molecular bonding of the sample biomolecule to the probe biomolecule. More specifically, the rotation unit 120 is immersed in a first specific solution in which the sample biomolecule to be analyzed has not been included. Once immersed in the first solution, rotation unit 120 is rotated by applying an input signal of a certain frequency and amplitude through the input port 140. A first rotational frequency $w_1$ is then determined (as shown at S230).

The first specific solution is then removed from the rotation unit 120 (S240). The first specific solution is replaced by a second specific solution which comprises the sample biomolecule to be analyzed (S250). In some embodiments, instead of injecting the second specific solution into the rotation unit 120, the rotation unit 120 can be directly immersed in a receptacle (not shown) containing the second specific solution. Generally, the apparatus is implemented by a microelectromechanical system (MEMS) structure in which a micro-pump and a micro-valve are installed in one structure so as to supply and discharge the second specific solution with respect to the rotation unit 120.

Once the second specific solution is supplied to the rotation unit 120, the rotation unit 120 is rotated, thereby mixing the probe biomolecule 130 and the sample biomolecule 132 in the second specific solution such that binding between the sample biomolecule and the probe biomolecule 130 immobilized on the rotation unit 120 can occur (S260).

FIG. 4B illustrates mixing of the probe biomolecule 130 with sample components (132 and 134) of the second specific solution. Sample biomolecule 132 has properties that permit binding with the probe biomolecule 130, and therefore molecular bonding occurs between sample biomolecule 132 and probe biomolecule 130.

After a predetermined time, a sample component 134 not bonded with the probe biomolecule 130 in the second specific solution is removed by injecting a wash solution into the rotation unit 120, as shown in FIG. 4C (S270).

After the removing the second specific solution (and any unbound sample components 134) from the rotation unit 120, the rotational frequency of the rotation unit 120 is measured again. The rotational frequency is measured in the same manner as when the rotational frequency of the rotation unit 120 was measured before the binding reaction. The rotational frequencies of the rotation unit 120 before and after mixing the probe biomolecule 130 with the sample biomolecule 132 may then be compared to determine if molecular bonding has occurred. In one embodiment, following removal of the second specific solution, the rotation unit 120 is rotated in the first specific solution for measuring a second rotational frequency $w_2$ (S280). The second frequency $w_2$ represents the frequency of rotation unit 120 following mixing of the probe biomolecule 130 with the sample biomolecule 132.

Finally, the determination of whether the molecular bonding is achieved is made by comparing rotational frequencies $w_2$ and $w_1$, the rotational frequencies measured after and before the possible biomolecular bonding, respectively (S290). Different values for rotational frequencies $w_2$ and $w_1$ indicate that molecular bonding occurred between the probe biomolecule 130 and the sample biomolecule 132. The magnitude of the difference between the first and second rotational frequencies $w_1$ and $w_2$ can further provide information on the presence and extent of molecular bonding.

As can be appreciated from the above description, the apparatus and methods for detecting the biomolecular bonding disclosed herein allow for the detection of the presence and extent of molecular bonding by measuring any difference between the rotational frequencies $w_2$ and $w_1$ before and after mixing the probe biomolecule 130 immobilized to the rotation unit 120 with the sample biomolecule 132. As such, the need for expensive frequency detecting devices such as a laser is obviated. Also, the detection method can be considerably simplified since molecular bonding can be detected by directly immersing the biomolecular detecting apparatus of the present invention in the specific solution that includes the sample biomolecule 132.

FIG. 6 is a flowchart illustrating a method for detecting the biomolecular-bonding, according to another embodiment of the present invention.

As is shown, the rotation unit 120 is mounted on a predetermined area of the substrate 110 (S310). One or more probe biomolecules 130 are immobilized on the rotation unit 120 (S320).

The rotation unit 120 can be immersed in the first specific solution wherein the sample biomolecule to be analyzed has not been included. The rotation unit 120 is driven by applying an input signal having a certain frequency and amplitude through the input port 140. Upon driving the rotation unit 120, a first rotational frequency $w_1$ of the rotation unit 120 is measured (S330). The first specific solution can be removed (S340) and the second specific solution which comprises the sample biomolecule to be analyzed is supplied to the rotation unit 120 (S350). In this embodiment as well as previous ones, instead of injecting the second specific solution into the rotation unit 120, the rotation unit 120 may be directly immersed in a container (not shown) having therein the second specific solution.

Any changes of the rotational frequency are monitored while mixing the sample biomolecule in the second specific solution and the probe biomolecule by driving the rotation unit 120 in the second specific solution (S360) and then measuring the rotational frequency.

In summary, the determination of whether molecular bonding between the probe biomolecule and a sample biomolecule has occurred can be detected by monitoring the rotational frequency of the rotation unit 120. If the rotational frequency does not change while driving the rotation unit 120, it is determined that molecular bonding has not occurred, and therefore a sample biomolecule that bonds to the probe molecule is not present in the second specific solution. If the rotational frequency gradually changes, it is indicative that molecular bonding is occurring and therefore, a sample biomolecule that binds to the probe molecule is included in the second specific solution.

As described above, the embodiments of the present invention include an apparatus and method for detecting biomolecular-bonding. Molecular bonding is detected by measuring the difference of the rotational frequency of the rotation unit 120 before and after bonding between a probe biomolecule 130 and the sample biomolecule has occurred. As a result, neither high-priced detectors, such as a laser, nor a dedicated labeling reaction as used in detecting methods which uses fluorescent material are required. In addition, the embodiments of the present invention provide a simple method for detecting biomolecular bonding through directly immersing the detecting apparatus in the specific solution which includes the sample biomolecule.

The foregoing embodiment and advantages are merely exemplary and are not to be construed as limiting the present invention. While the invention has been shown and described with reference to certain embodiments thereof, it will be understood by those skilled in the art that various changes in form and details may be made therein without departing from the spirit and scope of the invention as defined by the appended claims.

What is claimed is:

1. An apparatus for detecting biomolecular bonding, comprising:
    a substrate;
    a rotation unit, wherein the rotation unit comprises a support part mounted on the substrate and a pillar part vertically protruding from the support part, the pillar part having an immobilized probe biomolecule on a surface thereof;
    an input port connected to the substrate, the input port configured to receive an input signal for driving the rotation unit;
    an output port connected to the substrate, the output port configured to output an output signal indicative of the rotational frequency of the rotation unit; and
    a frequency detector in communication with the output port to detect a change in a frequency of the rotation unit generated by a change in torsional vibration of the rotation unit in order to determine the presences or absence of bonding between the probe biomolecule and a sample biomolecule.

2. The apparatus of claim 1, wherein the rotation unit rotates unidirectionally about a shaft.

3. The apparatus of claim 1, wherein the rotation unit rotates bidirectionally about a shaft.

4. The apparatus of claim 2, wherein the substrate is equipped with a motor that drives rotation of the rotation unit.

5. The apparatus of claim 2, wherein the rotation unit is equipped with a rotor.

6. The apparatus of claim 1, wherein the rotation unit is immobilized on the substrate by one end thereof and is torsionally vibrated upon application of the input signal from the input port.

7. The apparatus of claim 6, wherein the rotation unit comprises a piezoelectric material.

8. The apparatus of claim 1, wherein the probe biomolecule comprises at least one of a deoxyribonucleic acid (DNA), a ribonucleic acid (RNA), a protein, a cell, a nucleic acid, enzyme, or a combination thereof.

9. The apparatus of claim 1, wherein the pillar part has a cylindrical or a polygonal-pillar shape.

10. A method for biomolecular bonding, comprising:
    providing the apparatus for detecting biomolecular bonding of claim 1;
    driving the rotation unit and measuring a first rotational frequency $W_1$ of the rotation unit mixing the probe biomolecule and a sample biomolecule;
    driving the rotation unit and measuring a second rotational frequency $W_2$ of the rotation unit after mixing the probe biomolecule with the sample biomolecule; and
    determining the presence or absence of bonding between the probe biomolecule and the sample biomolecule by comparing the first and second rotational frequencies $W_1$ and $W_2$.

11. The method of claim 10, wherein the first and second rotational frequencies $w_1$ and $w_2$ of the rotation unit are measured by driving the rotation unit in a first specific solution in which the sample biomolecule is not included.

12. The method of claim 11, wherein the mixing further comprises:
    removing the first specific solution from the rotation unit;
    supplying a second specific solution which comprises the sample biomolecule to the rotation unit; and
    driving the rotation unit such that bonding can occur between the probe biomolecule and the sample biomolecule.

13. The method of claim 12, further comprising cleaning any biomolecules not bonded to the probe biomolecule.

14. A method for detecting biomolecular bonding, comprising:

providing the apparatus for detecting biomolecular bonding of claim 1;

measuring a first rotational frequency $W_1$ of the rotation unit before bonding, by driving the rotation unit in a first specific solution in which a sample biomolecule is not included;

mixing the probe biomolecule with the sample biomolecule by driving the rotation unit in a second specific solution comprising the sample biomolecule, and measuring a second rotational frequency $W_2$ of the rotation unit after mixing the probe biomolecule with the sample biomolecule; and comparing the first and second rotational frequencies $W_1$ and $W_2$ to detect biomolecular bonding.

15. The method of claim 14, further comprising removing the first specific solution after measuring the first rotational frequency $w_1$.

* * * * *